United States Patent

Ong et al.

[11] Patent Number: 4,496,582
[45] Date of Patent: Jan. 29, 1985

[54] ANALGESIC DIBENZ[B,F]OXEPINS

[75] Inventors: Helen H. Ong, Whippany; Matthew J. Flynn, North Plainfield, both of N.J.

[73] Assignee: Hoechst-Roussel Pharmaceuticals Incorporated, Somerville, N.J.

[21] Appl. No.: 560,717

[22] Filed: Dec. 12, 1983

[51] Int. Cl.³ .................. A61K 31/335; C07D 313/14
[52] U.S. Cl. ..................... 514/450; 549/354
[58] Field of Search ........................ 549/354; 424/278

[56] References Cited

PUBLICATIONS

P. Cagniant et al., C. R. Acad. Sc. Paris, Ser. C, vol. 283 (Dec. 8, 1976), pp. 683–686.

*Primary Examiner*—Norma S. Milestone
*Attorney, Agent, or Firm*—Tatsuya Ikeda

[57] ABSTRACT

There are described analgesic dibenz[b,f]oxepins having the general formula

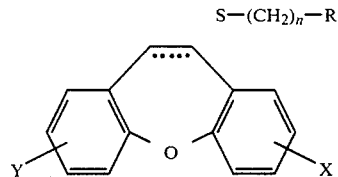

wherein n is an odd integer 1–7 inclusive; R is $-CO_2R_1$ or $-CH_2OR_2$ where $R_1$ is H, $C_{1-5}$ lower alkyl, aralkyl,

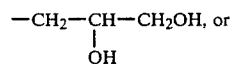

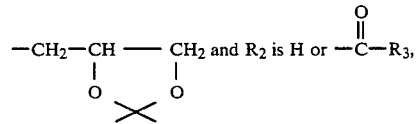

$R_3$ being $C_{1-5}$ lower alkyl; X and Y are each independently hydrogen, halogen, trifluoromethyl, $C_{1-5}$ lower alkoxy, $C_{1-5}$ lower alkyl, $C_{1-5}$ lower alkylthio, or hydroxy; and the dotted line   may be a bond or nothing.

38 Claims, No Drawings

ANALGESIC DIBENZ[B,F]OXEPINS

This invention relates to novel analgesic dibenz[b,f]oxepins of the general formula

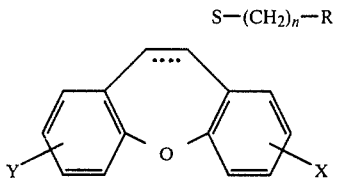

wherein n is an odd integer 1–7 inclusive; R is $-CO_2R_1$ or $-CH_2OR_2$ where $R_1$ is H, $C_{1-5}$ lower alkyl, aralkyl, $-CH_2-CH-CH_2OH$, or
      |
      OH

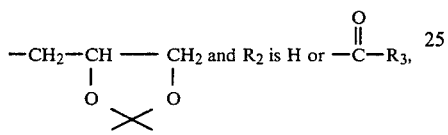

$R_3$ being $C_{1-5}$ lower alkyl; X and Y are each independently hydrogen, halogen, trifluoromethyl, $C_{1-5}$ lower alkoxy, $C_{1-5}$ lower alkyl, $C_{1-5}$ lower alkylthio, or hydroxy; and the dotted line ⋯⋯ may be a bond or nothing.

To the best of our knowledge the compounds of the present invention have not been described or suggested.

Throughout the specification and the appended claims, a given chemical formula or name shall encompass all stereo isomers thereof where such isomers exist. The term "halogen" shall mean fluorine, chlorine or bromine. The term "aralkyl" shall mean $C_{1-5}$ lower alkyl having an unsubstituted or substituted phenyl group.

The compounds of the present invention are prepared by following one or more of the steps described below in which the definitions of n, R, $R_1$, $R_2$, $R_3$, X and Y are as defined above unless noted to the contrary.

STEP A

A 10,11-dihydro-10-oxodibenz[b,f]oxepin of Formula II is reacted with a compound of the formula HS-$(CH_2)_n$-R to afford a compound of this invention having Formula III.

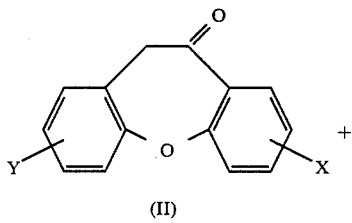

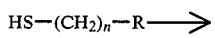

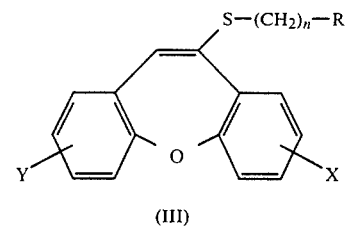

This reaction is carried out with a catalyst/dehydrating agent of boron trifluoride etherate and in the presence of a suitable solvent such as glacial acetic acid at a temperature of about ambient to reflux for a suitable length of time, a typical example being 3 hours at 65° C.

STEP B

Compounds III prepared in STEP A are reduced to the corresponding 10,11-dihydro derivatives thereof in the presence of magnesium metal and a loweralkanol.

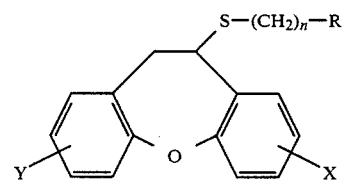

The reduction is conveniently performed by dissolving or suspending Compound III in a loweralkanol, adding magnesium metal in a suitable form and allowing the reaction to proceed for a period of time necessary for the substantial reduction of the double bond. Appropriate loweralkanols include those having from 1 to 6 straight or branched chain carbon atoms such as, for example, methanol, ethanol, 1-propanol, 2-propanol, 2-methyl-2-propanol, pentanol, 3-methyl-3-pentanol and the like. Methanol is preferred. Suitable forms of magnesium metal include pellets, grindings, shavings and the like. Shavings are preferred.

While the reaction temperature is not narrowly critical, it is desirable to perform the reaction at a temperature such that the reduction proceeds at a reasonable rate. Reaction temperatures between about ambient (25° C.) and about 50° C. accomplish this object.

All other starting materials shown above are either known compounds or easily prepared by routine methods known to the art from readily available materials.

Compounds of Formula I of the present invention are useful as analgesic agents due to their ability to alleviate pain in mammals. The activity of the compounds is demonstrated in the 2-phenyl-1,4-benzoquinone-induced writhing test in mice, a standard assay for analgesia [Proc. Soc. Exptl. Biol. Med., 95, 729 (1957)]. Thus, for instance, 11-[beta-(carboxymethyl)thio]-2-fluorodibenz[b,f]oxepin displayed an $ED_{50}$ of 16.8 mg/kg sc in the phenylquinone writhing assay for analgesia.

Effective quantities of the compounds of the invention may be administered to a patient by any of the various methods, for example, orally as in capsules or tablets, parenterally in the form of sterile solutions or suspensions, and in some cases intravenously in the form of sterile solutions. The free acid final products, while effective themselves, may be formulated and administered in the form of their pharmaceutically acceptable addition salts for purposes of stability, convenience of crystallization, increased solubility and the like.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspension may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include 11-[beta-(Carboxymethyl)thio]-2-fluorodibenz[b,f]oxepin;

11-[beta-(Carboxymethyl)thio]-2-chlorodibenz[b,f]oxepin; and

11-[beta-(Carboxymethyl)thio]-7-chloro-2-fluorodibenz[b,f]oxepin.

The following examples are given for illustrative purposes and are not to be considered as limiting the invention disclosed herein.

EXAMPLE 1

11-[beta-(Carboxymethyl)thio]-2-fluorodibenz[b,f]oxepin

A mixture prepared from 4.5 g (20 mmole) of 2-fluoro-10,11-dihydro-11-oxodibenz[b,f]oxepin and 1.8 g of mercaptoacetic acid in 10 ml of glacial acetic acid containing 4.5 ml of boron trifluoride etherate was stirred at 65° C. for 3 hours under nitrogen atmosphere. The solution after cooling was diluted with 200 g of ice-water, extracted with ether (2×300 ml) and the combined ether solution was shaken with 20% NaOH. A precipitate was separated, washed with ether and acidified to pH 2 with 20% HCl. The acid was taken up in ether (2×300 ml), washed exhaustively with water and dried. Evaporation of solvent in vacuo left a material which was chromatographed on a column of silica gel packed in $CH_2Cl_2$. Elution with methanol/$CH_2Cl_2$ (80:20) afforded a solid which was transferred to a brown bottle with the aid of a small amount of ether. This material crystalized on standing, m.p. 105°–107° C. It was dried for 48 hours at 100° C. and 0.2 mm Hg pressure.

| ANALYSIS: | | |
|---|---|---|
| Calculated for $C_{16}H_{11}FO_3S$: | 63.56% C | 3.68% H |
| Found: | 63.35% C | 3.84% H |

EXAMPLE 2

11-[beta-(Carboxymethyl)thio]-2-chlorodibenz[b,f]oxepin

A mixture prepared from 2-chloro-10,11-dihydro-11-oxodibenz[b,f]oxepin (3.0 g, 12.3 mmoles) and 1.8 g of mercaptoacetic acid in 10 ml of glacial acetic acid containing 4.5 ml of boron trifluoride etherate was heated and stirred at 70° C. for 2½ hours. The cooled solution was diluted with water (about 200 ml), extracted with ether and the combined ether solution was shaken with 20% NaOH. The precipitate was filtered, washed with water and ether and acidified to pH=2 with 10% HCl. Ether (300 ml) was added to take up the liberated acid. After stirring at room temperature for 30 minutes, the ether layer was separated, washed twice with water and dried over $MgSO_4$. Evaporation of solvent afforded a solid which was recrystallized from ether/hexane to give crystals, m.p. 143°–145° C. The yield was 2.3 g (64%).

| ANALYSIS: | | |
|---|---|---|
| Calculated for $C_{16}H_{11}ClO_3S$: | 60.28% C | 3.48% H |
| Found: | 60.35% C | 3.60% H |

EXAMPLE 3

11-[beta-(Carboxymethyl)thio]-7-chloro-2-fluorodibenz[b,f]oxepin

A mixture prepared from 7-chloro-2-fluoro-10,11-dihydro-11-oxodibenz[b,f]oxepin (3.0 g, 0.011 mole) and 1.8 g of mercaptoacetic acid in 10 ml of glacial acetic acid containing 4.5 ml of boron trifluoride etherate was stirred at 65° for 4 hours under nitrogen. The cooled reaction mixture was quenched with 200 ml of ice-water and extracted three times with ethyl ether. The combined ether solution was shaken with 20% NaOH to give a heavy precipitate which was removed by filtration. After washing with ether, the solid precipitate was acidified with an ice-cold solution of 20% HCl, and the separated oil was again taken into ether. Evaporation of this solution after drying over $MgSO_4$ left a crystalline solid which was passed through a column of silica gel packed in hexane, using a solution of 20% methanol/$CH_2Cl_2$ as the eluent. The fractions containing the major product (silica gel, 20% methanol-$CH_2Cl_2$, Rf=0.73) were pooled to give 1.8 g (48.5%) of a crude product. This material was dissolved in acetone, and treatment of the acetone solution with hexane (just long enough to cause a permanent turbidity) deposited a solid which appeared to contain a polar solvent and other impurities. Evaporation of the filtrate afforded the pure acid, m.p. 146°–147° C.

| ANALYSIS: | | |
|---|---|---|
| Calculated for $C_{16}H_{10}ClFO_3S$: | 57.06% C | 2.99% H |
| Found: | 57.53% C | 3.19% H |

We claim:

1. A compound depicted by the formula

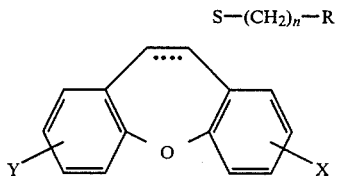

wherein n is an odd integer 1–7 inclusive; R is $-CO_2R_1$ or $-CH_2OR_2$ where $R_1$ is H, $C_{1-15}$ lower alkyl, aralkyl,

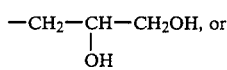

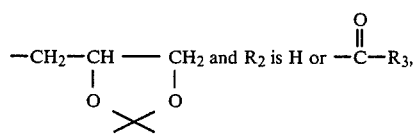

$R_3$ being $C_{1-5}$ lower alkyl; X and Y are each independently hydrogen, halogen, trifluoromethyl, $C_{1-5}$ lower alkoxy, $C_{1-5}$ lower alkyl, $C_{1-5}$ lower alkylthio, or hydroxy; and the dotted line ( ) may be a bond or nothing.

2. The compound as defined in claim 1, where the dotted line is a bond.

3. The compound as defined in claim 2, where Y is hydrogen.
4. The compound as defined in claim 3, where X is fluorine.
5. The compound as defined in claim 3, where X is chlorine.
6. The compound as defined in claim 3, where X is hydrogen.
7. The compound as defined in claim 2, where n is 1.
8. The compound as defined in claim 7, where R is $-CO_2H$.
9. The compound as defined in claim 8, where Y is hydrogen.
10. The compound as defined in claim 9, where X is fluorine.
11. The compound as defined in claim 10, which is 11-[beta-(carboxymethyl)thio]-2-fluorodibenz[b,f]oxepin.
12. The compound as defined in claim 9, where X is chlorine.
13. The compound as defined in claim 12, which is 11-[beta-(carboxymethyl)thio]-2-chlorodibenz[b,f]oxepin.
14. The compound as defined in claim 9, where X is hydrogen.
15. The compound as defined in claim 2, where Y is chlorine.
16. The compound as defined in claim 15, where X is fluorine.
17. The compound as defined in claim 15, where X is chlorine.
18. The compound as defined in claim 15, where X is hydrogen.
19. The compound as defined in claim 15, where n is 1.
20. The compound as defined in claim 19, where R is $-CO_2H$.
21. The compound as defined in claim 20, where X is fluorine.
22. The compound as defined in claim 21, which is 11-[beta-(carboxymethyl)thio]-7-chloro-2-fluorodibenz[b,f]oxepin.
23. The compound as defined in claim 20, where X is chlorine.
24. The compound as defined in claim 20, where X is hydrogen.
25. The compound as defined in claim 1, where the dotted line is not a bond.
26. The compound as defined in claim 25, where n is 1.
27. The compound as defined in claim 26, where R is $-CO_2H$.
28. The compound as defined in claim 27, where Y is hydrogen.
29. The compound as defined in claim 28, where X is fluorine.
30. The compound as defined in claim 28, where X is chlorine.
31. The compound as defined in claim 28, where X is hydrogen.
32. The compound as defined in claim 27, where Y is chlorine.
33. The compound as defined in claim 32, where X is fluorine.
34. The compound as defined in claim 32, where X is chlorine.
35. The compound as defined in claim 32, where X is hydrogen.

36. An analgesic composition which comprises an effective pain alleviating amount of a compound depicted by the formula

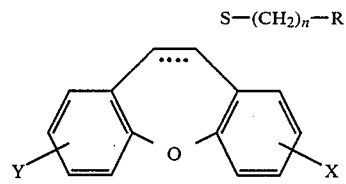

wherein n is an odd integer 1–7 inclusive; R is —CO$_2$R$_1$ or —CH$_2$OR$_2$ where R$_1$ is H, C$_{1-5}$ lower alkyl, aralkyl,

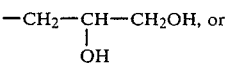

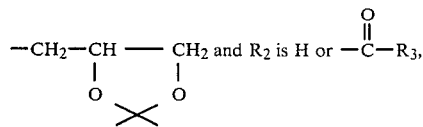

R$_3$ being C$_{1-5}$ lower alkyl; X and Y are each independently hydrogen, halogen, trifluoromethyl, C$_{1-5}$ lower alkoxy, C$_{1-5}$ lower alkyl, C$_{1-5}$ lower alkylthio, or hydroxy; and the dotted line ( ) may be a bond or nothing.

37. The analgesic composition as defined in claim 36, where the dotted line is a bond.

38. The analgesic composition as defined in claim 36, where the dotted line is not a bond.

* * * * *

UNITED STATES PATENT AND TRADEMARK OFFICE
CERTIFICATE OF CORRECTION

PATENT NO. : 4,496,582

DATED : January 29, 1985

INVENTOR(S) : Helen H. Ong; Matthew J. Flynn

It is certified that error appears in the above-identified patent and that said Letters Patent is hereby corrected as shown below:

On the title page:
In the Abstract (top of the right column):

Column 1, line 8; Column 5, Line 40; and Column 7, line 9, a solid line signifying a single bond should be drawn between the sulfur atom and the 11-th position of the fused ring.

Signed and Sealed this

Thirtieth Day of April 1985

[SEAL]

Attest:

DONALD J. QUIGG

Attesting Officer

Acting Commissioner of Patents and Trademarks